United States Patent [19]
Krumdieck

[11] Patent Number: 5,550,033
[45] Date of Patent: Aug. 27, 1996

[54] MOLD PLUNGER AND METHOD FOR EMBEDDING TISSUE SAMPLES

[76] Inventor: Carlos Krumdieck, 3408 Wellford Cir., Birmingham, Ala. 35216

[21] Appl. No.: 312,034

[22] Filed: Sep. 26, 1994

[51] Int. Cl.[6] .................................................. C12Q 1/08
[52] U.S. Cl. .................. 435/40.52; 435/283.1; 435/309.1; 422/102; 422/104; 425/117; 83/21; 83/25; 83/373; 83/401; 83/409; 83/422; 83/438; 83/444; 83/451; 83/648; 83/915.5
[58] Field of Search ................ 435/40.52, 287, 435/296; 422/102, 104; 425/117; 83/21, 25, 373, 401, 409, 422, 438, 444, 451, 648, 915.3

[56] References Cited

U.S. PATENT DOCUMENTS

| | | |
|---|---|---|
| 4,569,647 | 2/1986 | McCormick ............................ 425/117 |
| 4,647,543 | 3/1987 | Stöcker .................................. 436/174 |
| 4,752,347 | 6/1988 | Rada ....................................... 156/382 |
| 4,754,675 | 6/1988 | Segal ........................................ 83/437 |
| 4,914,022 | 4/1990 | Furmanski et al. ......................... 435/7 |
| 5,312,758 | 5/1994 | Ahlquist .................................. 436/63 |

*Primary Examiner*—David A. Redding
*Attorney, Agent, or Firm*—Veal & Marsh

[57] ABSTRACT

A method and apparatus for preparing tissue samples for subsequent slicing in a microtone, utilizing a thermally transmissive body and removable mold heads to facilitate encapsulation of tissue samples in a gelatinous substance so that the samples may be selectively oriented for proper slicing in the microtone.

15 Claims, 3 Drawing Sheets

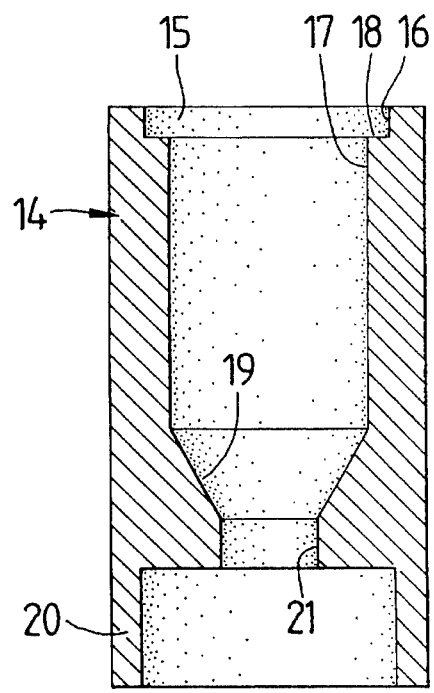
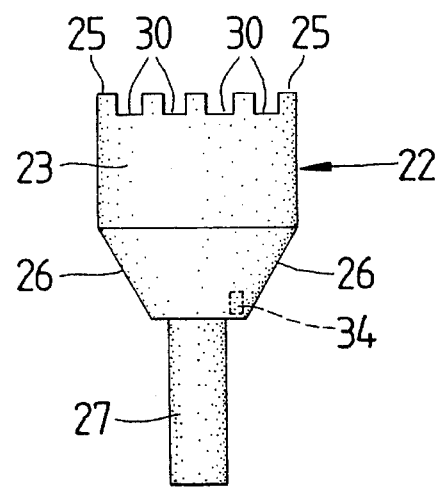
FIG. 2  FIG. 3
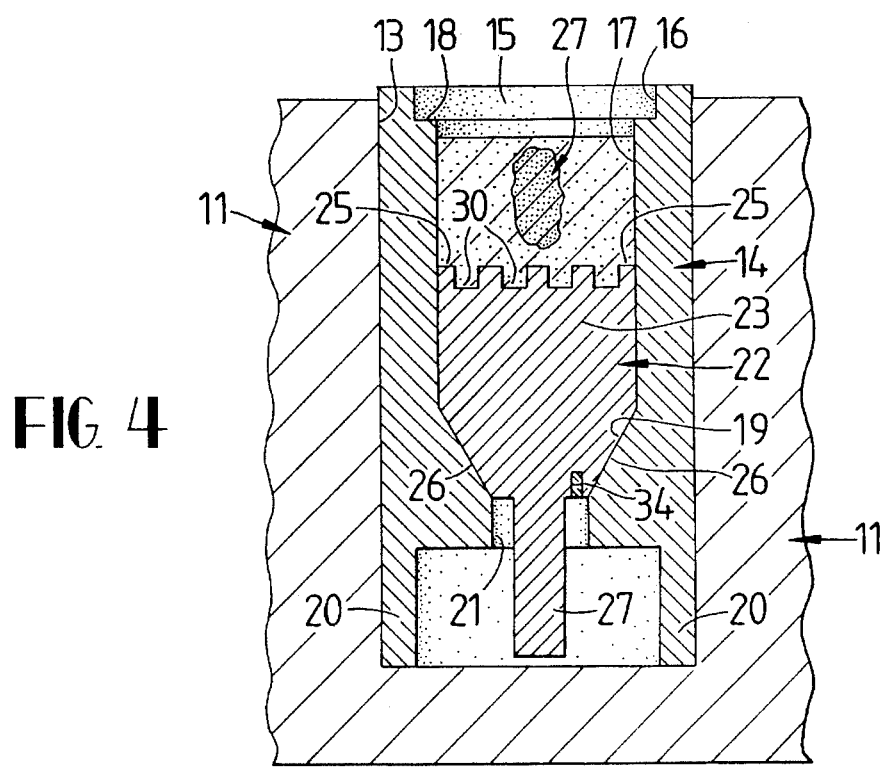
FIG. 4

MOLD PLUNGER AND METHOD FOR EMBEDDING TISSUE SAMPLES

FIELD OF THE INVENTION

This invention relates to an improved mold plunger for use with a biological tissue slicer designed to produce aseptic thin slices of tissue suitable for biochemical, pharmacological or toxicological studies. In greater particularity, the present invention relates to a mold plunger having a conical head insertable within a mold cavity. The head seals a lower opening in conical portion of the mold cavity providing a leak proof compartment for embedding a tissue sample within a gel.

BACKGROUND OF THE INVENTION

Tissue culture methodologies allow physiological reactions and occurrences to be studied outside the organism without the influence of other biological reactions.

Incubation of tissue slices for short periods (hours) was introduced for biomedical studies in 1923 by Warburg. Prolonged incubations (days/weeks) were, in practice, not possible until the 1950's, following the introduction of antibacterial and antifungal antibiotics.

There must be uniformity between individual tissue sample for uniformity and reproducibility among experiments for an effective tissue culture methodology. In the past, the production of homogeneous tissue slices from fresh tissue samples has been difficult and dependent on the skill and the experience of the technician. Attempts to produce tissue samples which are uniform in dimension have been met with problems including irreproducibility of slice thickness, contamination of tissue samples and irregular, nonreproducible trauma to the tissue adjacent to the cutting surface.

In U.S. Pat. No. 5,148,729, the applicant disclosed a biological tissue slicer which allowed an inexperienced technician to produce nearly identical tissue slices in an aseptic environment while minimizing tissue trauma. The invention included a blade held in a blade holder between two pins while one or more permanent magnets provide a constant downward pull on the blade and blade holder. The design eliminated need for readjustment or tightening which are opportunities for contamination. The reproducibility of tissue slices is increased as vertical "chatter" of the blade decreases. Also, the exposure of the tissue sample to the blade is limited to reduce the extent of trauma to the cut surface of the tissue.

Also it is difficult to obtain proper slices from very small samples, which may consist of an entire organ from an experimentally sacrificed animal, for example.

A common practice in sampling tissue involves cutting a cylindrical core from an organ or quantity of tissue with a coring tool or similar device. The cylindrical core, however, leaves a large amount of tissue in between the cores which is unusable for slicing.

An often overlooked factor for obtaining quality tissue slices is the proper orientation of the tissue sample within the slicing machine. Coring cylinders from some tissues, for example, liver, usually result in major blood vessels being oriented parallel to the plane of slicing. When thus oriented, the cutting blade of the tissue slicer comes in tangential contact with the tough connective tissue of the blood vessel wall and often fails to cut it, shredding instead the remainder of the slice. The vessels extend across the bottom of the core as the blade cuts pieces of tissue about the large longitudinal ridge of connective tissue formed across the lower surface of the core. This results in high quality cuts from the first 3 to 4 slices of a core but all subsequent cuts are shredded or contain holes, thus providing slices of poor quality. On the other hand, if it were possible for the tissue block to be oriented such that the major blood vessels are perpendicular to the plane of sectioning, slices of much better quality can be obtained. An improved method for preparing tissue is needed to yield usable tissue samples of sufficient quality so as to aid research in the biochemical, pharmacological and toxicological sciences.

SUMMARY OF THE INVENTION

It is an object of this invention to provide a mold plunger device for providing optimal support and the best possible orientation to tissue fragments of any shape or dimension during the preparation of tissue slices by setting tissue samples in a gel medium.

Still another object of this invention is to provide an improved mold plunger which self-seals the lower portion of a mold.

Yet another object of this invention is to provide a method for orienting tissue within a gel casing which provides a quantity of desirable tissue slices.

Embedding a tissue sample within a gel, such as agarose, has been found by the inventor to improve the quality of sliced tissue samples. Tissue samples are placed in forming apparatus and are covered with a gel, a solution of agarose, or sodium alginate. The forming apparatus are then transferred to a metal block with appropriate perforations to receive the same to allow the gel to harden about the tissue sample. If sodium alginate is used, it is made to gel about the tissue by changing the salt to calcium alginate by the addition of an excess of calcium chloride.

The forming apparatus includes a cylindrical mold defining a cavity having a peripheral wall which narrows to form a truncated conical portion at the bottom thereof. Also provided is a plunger, which includes a head which tapers to an elongated stem such that the head defines, in part, a conic surface. This conic surface of the plunger rests sealingly with the truncated conical portion of the mold to prevent liquid leakage between the contact surface of the plunger and the mold.

A tissue sample must be properly cut and thus oriented within the mold cavity prior to embedding the sample in a gel. An improved method of sectioning a quantity of tissue for embedding with a gelatin includes cutting the tissue into regular shaped pieces. These sections can then be oriented in the cavity with the major vessels of the sample substantially parallel to a vertical axis of the mold cavity. Subsequently, as the encased tissue sample contacts the transversely moving blade of the tissue sampler, the vessels are cut transversely. The number of usable tissue slices cut from samples is increased by this method.

BRIEF DESCRIPTION OF THE DRAWINGS

Apparatus embodying features of the present invention are depicted in the accompanying drawings which form a portion of this disclosure and wherein:

FIG. 2 is a sectional view of a mold;

FIG. 3 is an elevational view of a plunger;

FIG. 4 is a sectional view of the mold at a cavity with plunger therein, both at rest in a cradle;

DESCRIPTION OF THE PREFERRED EMBODIMENT

Figure 1:
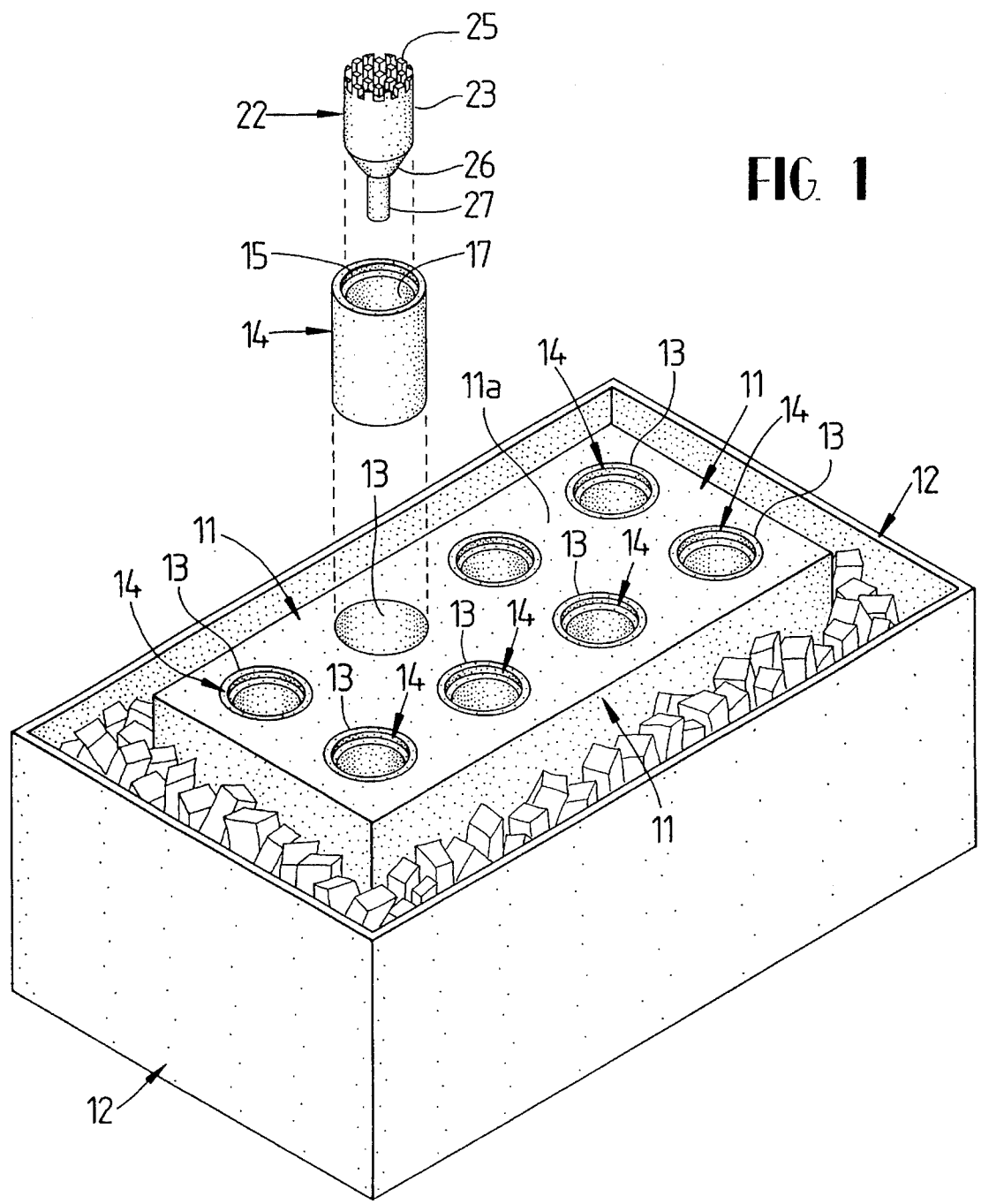
FIG. 1 is an exploded perspective view of the mold, plunger, and cradle.

Referring to the drawings for a clearer understanding of the invention, in FIG. 1 an improved forming apparatus for embedding samples is shown. A cradle 11, formed from aluminum or a suitable material, rests within an ice bath container 12. The cradle 11 has defined therein a number of vertical cavities 13 which extend downwardly from an upper surface 11a.

As shown in FIG. 1, each vertical cavity 13 receives therewithin a mold 14 which is externally matched to the inside dimension of the cavity 13. In FIG. 2, it may be seen that each mold 14 has a major diameter opening 15 defined by a first peripheral wall 16. A reduced diameter peripheral wall 17 is spaced from wall 16 to form a shoulder 18 above a cylindrical cavity section. Peripheral wall 17 terminates at its lower end in a truncated conical surface 19. A minor diameter opening 21 is defined in the bottom of mold 14. If needed, an annular flange 20 may surround the bottom of mold 14.

Insertable within the molds 14 is a mold plunger 22 which is likewise formed from aluminum or other suitable material. The mold plunger 22 includes a head 23 including an upper engaging surface 25 as shown in FIG. 3. This upper surface 25 may have longitudinal grooves or channels 30 defined therein to provide an optimum surface to bond with a gelatinous material. Each head 23 is generally cylindrical in shape; however, the outer surface tapers distal upper surface 25 to form a conic surface 26 to a depending stem portion 27. The plunger 22 has a magnet 34 mounted therein proximal the junction of the conic surface and the stem portion.

Referring now to FIG. 4, the plunger 22 and mold 14 are shown inserted within the cavity 13 of cradle 11. The stem 27 depends through and below the minor diameter opening 21. Note that the conic surface 26 of plunger head 23 rests snugly on the conic surface 19 of mold 14. The seal between surface 26 and surface 19 prevents liquid leakage from the mold 14. The upper engaging surface 25 of head 23 provides a false bottom to the mold 14 for accepting gel forming material in liquid form. The longitudinal channels 30 provide an uneven contact surface for improved bonding of gelatinous material to the plunger head 23 surface 25.

Figure 5:
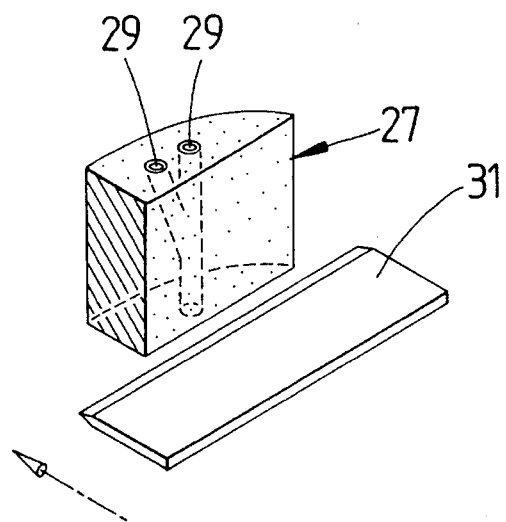
FIG. 5 is a perspective view of a tissue sample properly oriented relative to a slicing blade.

A tissue sample 27 suitable to be encased within a gelatinous material is retrieved from an organ using the following method. A core from an organ such as the lobe of a rat's liver is cut into nearly uniform pieces which may be oriented in the mold with major vessels 29 oriented such that the vessels 29 engage a cutting edge transversely, not longitudinally. Referring to FIG. 5, a cutting blade 31 of a microtone is shown cutting the vessels 29 transversely for clean consistent samples 40. Alternatively, a small organ such as a rat pituitary gland is removed from an experimentally sacrificed animal and placed on the plunger head for embedding and slicing.

In actual operation, the plungers 22 are inserted within mold 14 at room temperature. A tissue sample 27 is retrieved from an organ as described above. A piece of the sample 27 is placed on the tissue engaging surface 25 of plunger head 23 in a manner such that major vessels 29 are substantially parallel with the vertical axis of mold 14. A liquid gel material known in the art, such as agarose, is poured into the mold 14 and covers the tissue sample 27. The cradle containing the mold is placed in the ice bath container 12 and the gel is allowed to harden to a desired consistency.

Figure 6:
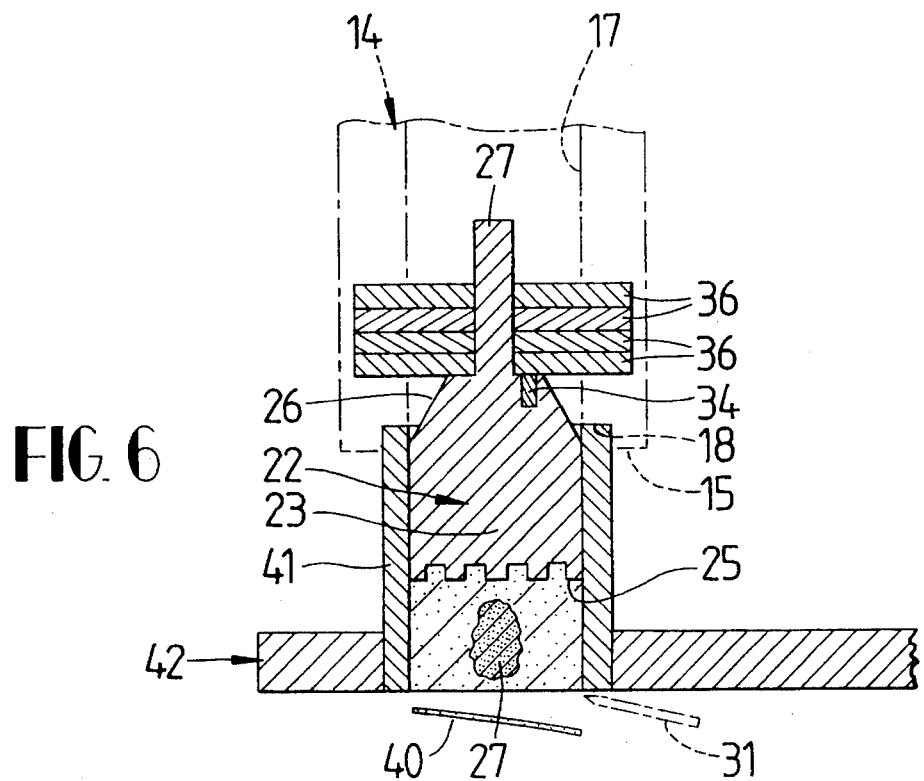
FIG. 6 shows a plunger and encased sample in a tissue slicing well.

When the agarose or other gel has reached the desired consistency, the mold 14, with the plunger, tissue sample and gel intact, is removed from the cradle and inverted over a tissue well 41 of a slicer 42, which is only partially shown in FIG. 6. The tissue well fits within major diameter walls of the mold such that shoulder 18 rests on the well structure and inner diameter walls 17 are essentially aligned with the inner walls of the tissue well. Pressure may be exerted on stem 27 to urge the plunger 22 out of the mold 14 into tissue well 41, and mold 14 may then be removed. A plurality of paramagnetic washers 36 are placed over stem 27 such that the magnet 34 can exert an attractive force thereon. The washers extend over the top of well 41 and are sufficiently attracted by the magnet 34 as to be able to support the plunger and tissue sample when the washers come to rest on top of the well. This serves to arrest the downward travel of the plunger by engaging the top of the tissue holding well of the slicer and preventing the plunger from protruding into the plane of sectioning once the tissue block has been completely cut into slices. Without this, the plunger would eventually hit the reciprocating blade of the slicer and dull the blade instantly. The washers 36 also add weight to the plunger to control downward force of the plunger 22 and gel encased pieces 27 into the tissue well 41 to engage the cutting surface.

The gel and tissues are sliced concurrently and are subsequently captured in a liquid bath. The temperature of the bath is then raised above the gelation temperature to release the tissue slices from the gel.

While I have shown my invention in one form, it will be obvious to one skilled in the pertinent art that it is not so limited, but is susceptible to various changes and modifications without departing from the spirit thereof.

What I claim is:

1. Apparatus for use in preparing tissue samples for subsequent sectioning into smaller portions comprising:
   a. at least one mold element defining an internal cavity which is open ended at an upper and lower end, generally cylindrical, and including an internal tapered region proximal said lower end thereof, said mold element being generally thermally transmissive; and
   b. removable sealing means insertable within said mold element in sealing relation with said tapered region for sealing said mold element against substantial egress of a liquid at said tapered region and for providing a tissue engaging surface, such that a tissue sample placed in said mold element superjacent said sealing means surface may be embedded within a gel forming fluid also placed in said cavity.

2. Apparatus as defined in claim 1 wherein said removable sealing means comprises an elongated metallic body having a major diameter cylindrical portion at one end thereof adapted for insertion within said mold cavity, a minor diameter cylindrical portion at an opposite end thereof adapted to extend through said cavity at said lower end and a conic region tapering from said major diameter cylindrical portion to said minor diameter cylindrical portion, and adapted to sealingly abut said tapered region of said cavity.

3. Apparatus as defined in claim 2 wherein said major diameter cylindrical portion terminates at said tissue engaging surface, said surface having a plurality of perpendicular grooves formed therein.

4. Apparatus as defined in claim 2 wherein said conic portion contains a magnetic material adjacent said minor diameter cylindrical portion.

5. Apparatus as defined in claim 4 further comprising a plurality of paramagnetic discs having a central aperture through which said minor diameter cylindrical portion may be inserted and having an outer diameter greater than said major diameter cylindrical portion.

6. Apparatus as defined in claim 1 wherein said mold element is insertable within a cradle for supporting one or more similar mold elements, each said mold element comprising:

(a) a uniform outer surface adapted for substantial abutting contact with said cradle;
   (b) an inner cylindrical surface having a major diameter portion proximal said upper end, and a minor diameter portion intermediate said major diameter portion and said tapered portion, there being a step intermediate said major and minor diameter portions.

7. Apparatus as defined in claim 1 wherein said mold element is made from a metal resistant to corrosion and thermal deformation at temperatures used to sterilize said mold element.

8. A method for making a plurality of tissue samples utilizing a microtome having a tissue well superjacent a slicing blade operatively configured to iteratively slice tissue in said well into uniform horizontally disposed slices comprising the steps of:

(a) obtaining at least one tissue sample of a size which will fit within said tissue well;
   (b) inserting a plunger head into a molding element to seal one end of an open ended cavity therein;
   (c) orienting said tissue sample on said plunger head within said cavity for a desired orientation of sections therethrough;
   (d) adding a selected gel forming substance to said cavity in sufficient quantity to cover said tissue sample;
   (e) allowing said gel forming substance to gel and unitize with said tissue sample and plunger head;
   (f) removing said plunger head, gel forming substance and tissue sample from said mold element as a unit, and inserting said unit into said tissue well with said tissue block proximal said slicing blade; and
   (g) iteratively slicing through said gelatinous substance and said tissue block to remove layers of tissue of a desired thickness.

9. The method of claim 8 further comprising placing said removed layers of tissue and gel in an aqueous solution at a temperature above the gelation temperature of said gelatinous substance to substantially separate said sliced layer of tissue therefrom.

10. The method of claim 8 wherein said orienting step comprises, identifying the orientation of vascular tissue within said tissue block and orienting said block such that said vascular tissue is cut transversely by said slicing blade during said slicing step.

11. An improved forming apparatus for use with a biological tissue slicer comprising:

(a) a mold element defining a generally cylindrical mold cavity which extends perpendicularly through said element from an upper end, said cavity narrowing to an opening in a lower end of said mold element; and
   (b) a plunger having a generally cylindrical head with a tissue engaging surface, said head tapering to a conical portion to a stem extending longitudinally from said head, said plunger being insertable within said mold cavity such that an outer surface of said tapering head engages the peripheral wall of said narrowing cavity to seal said bottom opening of said cavity.

12. An improved mold plunger as defined in claim 11 wherein said tissue engaging surface defines therein longitudinal grooves.

13. An improved mold plunger as defined in claim 12 wherein said plunger has a magnet integrally mounted proximal a junction of said inverted conical portion and said stem.

14. A method for encasing a tissue sample within a hardening medium for obtaining improved sample slices comprising:

(a) sizing a tissue sample to fit within a slicing well of a microtome;
   (b) orienting said tissue sample on an upper surface of a mold plunger resting within a mold cavity such that major vessels lie parallel to a center vertical line of said plunger;
   (c) covering said tissue sample with a gel forming medium and allowing said medium to harden; and
   (d) removing said mold plunger and said tissue sample encased within said gel as one unit and inverting said mold plunger into a tissue well of a tissue slicing machine, for iterative slicing thereof.

15. The method as defined in claim 14 further comprising using a magnetic stop member to engage said plunger to prevent contact of said plunger with a blade of said microtome.

* * * * *